United States Patent [19]
Pang et al.

[11] Patent Number: 5,299,457
[45] Date of Patent: Apr. 5, 1994

[54] PRECISION GRIP METER

[76] Inventors: Donald Pang, 2648 Forrest Ct., Fremont, Calif. 94536; David K. Pang, 3624 Nichole Ave., Pleasanton, Calif. 94588

[21] Appl. No.: 912,311

[22] Filed: Jul. 13, 1992

[51] Int. Cl.⁵ ............................................. G01L 15/00
[52] U.S. Cl. .................................. 73/379.02; 482/47
[58] Field of Search ............ 73/379.02, 379.01, 379.03; 482/44, 47, 49; 128/774

[56] References Cited

U.S. PATENT DOCUMENTS

| | | |
|---|---|---|
| 468,154 | 2/1892 | McClure . |
| 1,136,481 | 4/1915 | Ostrovsky ............................ 482/47 |
| 1,718,413 | 6/1929 | Edwards . |
| 1,796,216 | 3/1931 | Petersson . |
| 2,708,367 | 5/1955 | Lusk . |
| 2,784,592 | 8/1953 | Newman . |
| 3,111,322 | 11/1963 | English .............................. 482/47 |
| 3,227,446 | 1/1966 | Minasola ............................ 482/47 |
| 3,447,415 | 6/1969 | Kime . |
| 3,606,316 | 9/1971 | Krewer . |
| 3,738,651 | 6/1973 | Norman et al. . |
| 3,848,468 | 11/1974 | Richards . |
| 4,337,780 | 7/1982 | Metrick . |
| 4,553,746 | 11/1985 | Lee . |
| 4,592,371 | 6/1986 | Pellicano et al. . |
| 4,632,383 | 12/1986 | Tsuzuki . |
| 4,647,038 | 3/1987 | Noffsinger ........................ 482/106 |
| 4,674,330 | 6/1987 | Ellis . |
| 4,678,181 | 7/1987 | Ditsch et al. . |
| 4,742,832 | 5/1988 | Kauffmann et al. . |
| 4,824,103 | 4/1989 | Smidt . |
| 4,884,445 | 12/1989 | Sadoff et al. . |
| 4,886,073 | 12/1989 | Dillon et al. . |
| 4,949,729 | 8/1990 | Haski . |
| 5,147,256 | 10/1992 | Silagy ................................ 482/47 |

FOREIGN PATENT DOCUMENTS

| | | |
|---|---|---|
| 2060208 | 6/1972 | Fed. Rep. of Germany . |
| 3630438 | 3/1988 | Fed. Rep. of Germany . |
| 152331 | 5/1962 | U.S.S.R. . |
| 607118 | 5/1978 | U.S.S.R. . |

OTHER PUBLICATIONS

Scott, Cycling Art, Energy and Locomotion, (1889).

Primary Examiner—Richard E. Chilcot, Jr.
Assistant Examiner—R. Biegel
Attorney, Agent, or Firm—Ostrolenk, Faber, Gerb & Soffen

[57] ABSTRACT

A precision grip meter includes a frame; a base on the frame sized and shaped to engage the palm of the hand; a plurality of plungers on the frame opposite the base and located for being depressed by corresponding fingers of the hand; and a device associated with the base and the plungers for simultaneously measuring and recording both finger strength and overall hand strength. The grip meter may also comprise a frame; a force-detecting device; a first system on the frame for receiving the fingers of a hand and applying force exerted by the fingers to the force-detecting device; and a second system on the frame for receiving the heel of the hand and applying force exerted by the heel to the force-detecting device. Preferably, the grip meter is symmetrical so that it can be used for measuring the finger and hand strength of either the left hand or the right hand.

10 Claims, 4 Drawing Sheets

PRECISION GRIP METER

BACKGROUND OF THE INVENTION

The present invention relates to a device for measuring both hand and individual finger strength and, more particularly, to a device which can measure both hand and individual finger strength simultaneously.

DESCRIPTION OF RELATED ART

Hand grip devices have been used in the past for exercise. U.S. Pat. No. 3,738,651 and U.S. Pat. No. 4,678,181 relate to devices for exercising hand muscles. The devices have separate spring-loaded plungers for each finger. Resistance to finger pressure can be varied by replacing springs attached to the plungers.

U.S. Pat. No. 1,796,216 discloses a device for exercising the fingers which consists of two handgrips and four keys mounted on one of the handgrips for receiving the fingers. One set of springs exercises the user's fingers via the keys, and another set of springs exercises the hand as a whole.

These devices are for exercising the hand and fingers and not for measuring the pressure exerted by either the hand or the fingers.

Devices for measuring pressure exerted by a user have been disclosed in the prior art. U.S. Pat. No. 4,824,103 discloses an electronic system, consisting of an electromechanical force transducer or a load cell and a control processor unit, for recording the pressure exerted by a user on a device attached to the transducer unit. FIGS. 22-24 disclose a device for recording finger or hand pressure.

U.S. Pat. No. 4,884,445 discloses of a conventional Jamar dynamometer to include an electromechanical force transducer for producing output signals, which can be analyzed by a microcomputer to attempt to indicate both manual force and the subjective sincerity with which the manual force is applied.

All prior art materials cited herein are incorporated by reference.

The foregoing publications do not disclose or suggest a device or method for measuring both overall hand strength and the strength of the individual fingers simultaneously.

Further, the disclosed devices are excessively complex, bulky, and expensive.

SUMMARY OF THE INVENTION

Accordingly, it is an object of the present invention to provide a precision grip meter that can measure both hand strength and the strength of the individual fingers simultaneously.

Another object is to provide a grip strength meter that is easier and quicker to use and less complex, bulky and expensive than equipment known previously.

A further object is to provide for the use of a pressure-sensitive film as a force sensor in a grip meter for measuring both hand and individual finger strength.

A further object is to provide a precision grip meter that can be used with either the left or the right hand.

It has been found that the above and other objects of the present invention are attained by a precision grip meter that includes a frame; a base on the frame sized and shaped to engage the palm of the hand; a plurality of plungers on the frame opposite the base and located for being depressed by corresponding fingers of the hand; and a device associated with the base and the plungers for simultaneously measuring and recording both finger strength and overall hand strength. The grip meter may also comprise a frame; force-detecting means; first means on the frame for receiving the fingers of a hand and applying force exerted by said fingers to said force-detecting means; and second means on the frame for receiving the heel of the hand and applying force exerted by said heel to said force-detecting means.

Preferably, the device is symmetrical so that it can be used for measuring the finger and hand strength of either the left hand or the right hand.

Other features and advantages of the present invention will become apparent from the following description of an embodiment of the invention, which refers to the accompanying drawings.

DETAILED DESCRIPTION OF AN EMBODIMENT OF THE INVENTION

Figure 1:
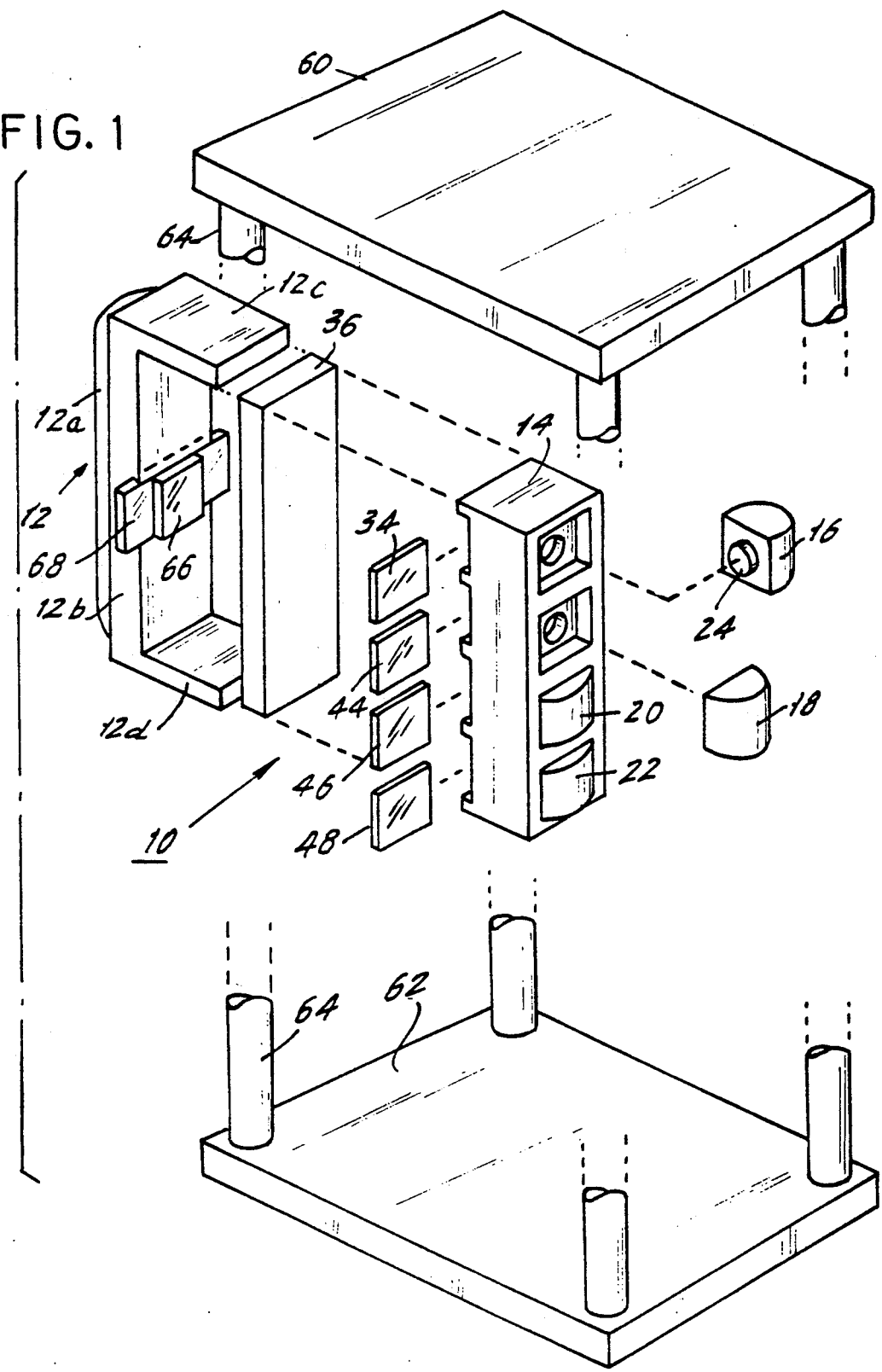
FIG. 1 is an exploded view of a precision grip meter according to an embodiment of the present invention.

Referring now to the drawings, FIG. 1 shows a precision grip meter 10.

The grip meter 10 includes a top support plate 60 and a bottom support plate 62 held together by shafts 64 to form a frame for the grip meter.

A base unit 12 adapted for receiving the heel of a hand comprises a rounded grip 12a, and a C-shaped unit including a vertical plate 12b and a pair of upper and lower flanges 12c and 12d which extend inward (with respect to the grip meter 10 as a whole). The top of the flange 12c and the bottom of the flange 12d are secured to the top and bottom support plates 60 and 62, respectively.

A plunger unit 14 is secured extending between the upper and lower flanges 12c, 12d by internal minimum-friction rails 13a, 13b (FIG. 2) of a conventional type, which enable the plunger unit 14 to glide within the C-shaped unit in one dimension with minimum friction, in addition to securing the plunger unit 14 to the flanges 12c, 12d. Four plungers 16, 18, 20 and 22 are mounted on the plunger unit 14, one for each individual finger. On the inner surfaces of the plungers are respective dowels 24, 26, 28 and 30. Inward from the dowels 24, 26, 28, 30 are respective strips of pressure-sensitive film 34, 44, 46, and 48.

The film strips are fixed to a cartridge 50 (FIG. 3A) having respective fingers 52, 54, 56, 58 for holding the film strips. The cartridge is preferably thin and rigid and the fingers are inserted into respective slots adjacent to the plunger unit 14, as shown in FIG. 1. The cartridge 50 should be inserted into the plunger unit 14 from the side opposite to the hand being tested so as not to interfere with the subject's grip.

Figure 2:
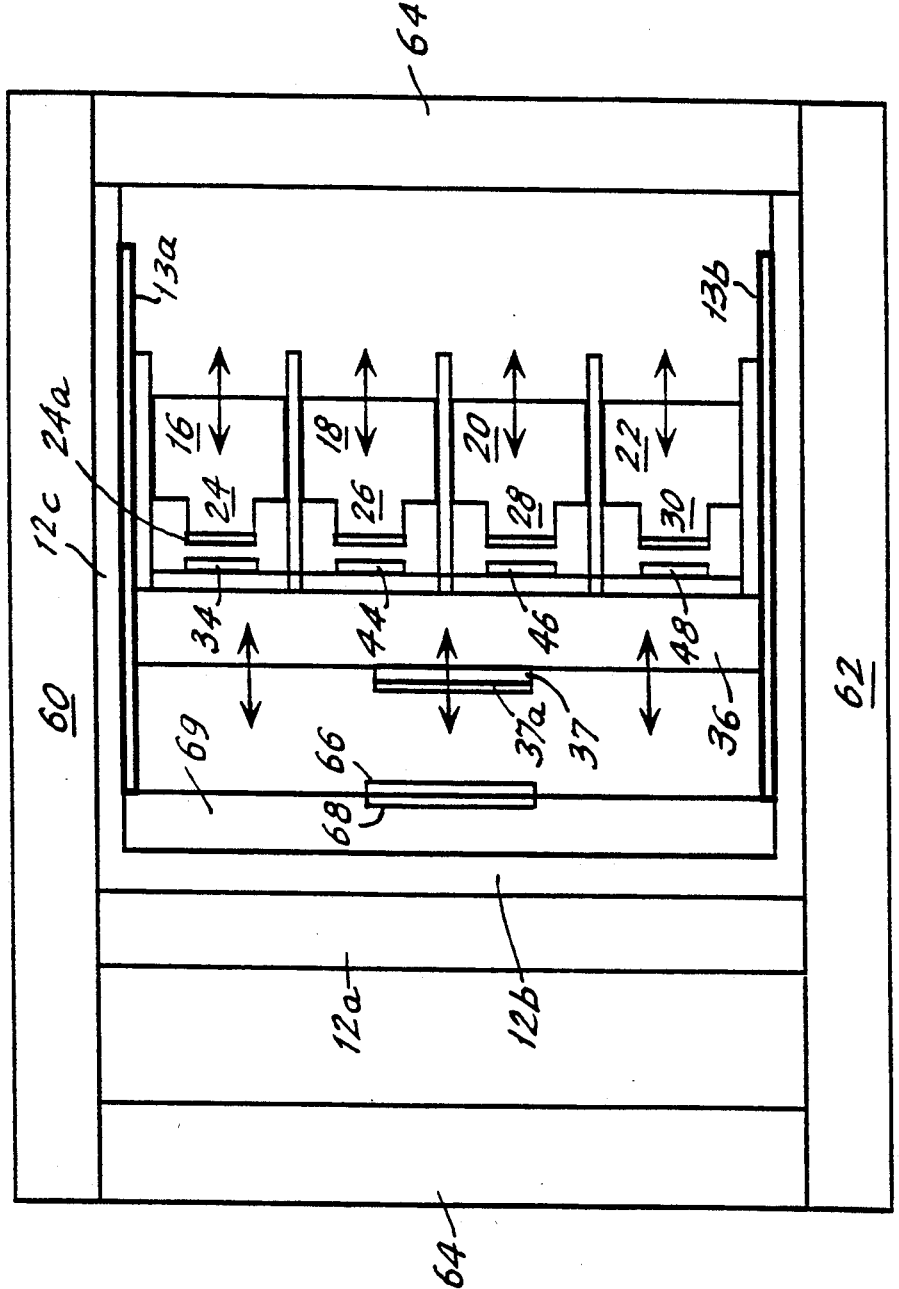
FIG. 2 is a cross-sectional side view of the precision grip meter.
Figure 3B:
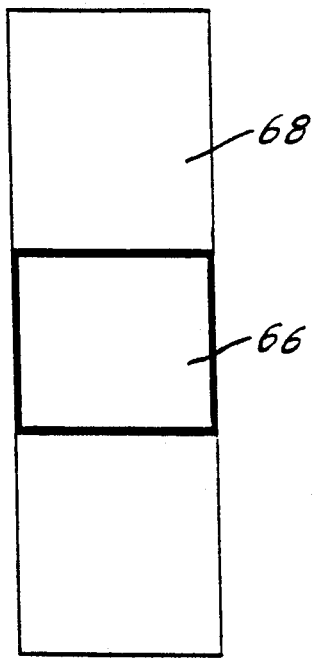
FIGS. 3A and 3B are schematic plan views illustrating pressure-sensitive films, and cartridges for placing the films adjacent the finger plungers and the base plunger of ,the precision grip meter of FIG. 1.
Figure 3A:
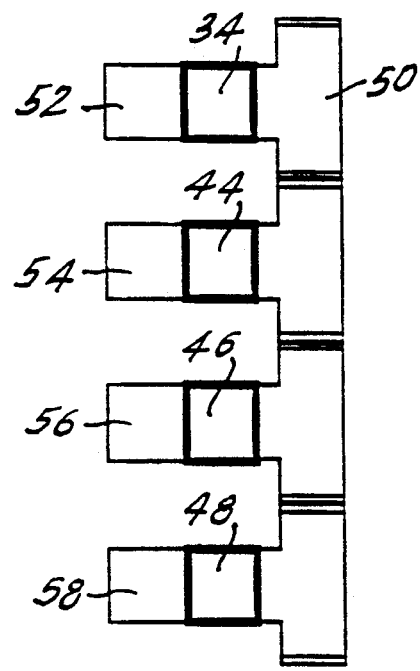

As seen in FIG. 2, the dowels are separated from the strips of film by gaps. A vertical plate 36 extends between the top and bottom flanges 12c, 12d and is secured substantially parallel to the plunger unit 14. The side of the vertical plate 36 away from the plunger unit 14 has a dowel 37. The dowel 37 opposes a second film cartridge 68 and a single film strip 66 which are mounted on a spacer 69, as shown in FIGS. 1, 2 and 3B.

To measure the strength of both the hand as a whole and the individual fingers, the grip meter is held with the base 12 against the heel of the subject's hand, and the plungers 16, 18, 20, 22 against the individual fingers. The subject grips the meter and thereby applies pressure against both the plungers and the base. Each of the dowels 24,26,28,30 is thereby urged against the corresponding film strip 34,44,46 and 48 with a pressure corresponding to the strength of the corresponding finger. Likewise, the dowel 37 associated with the base 12 is urged against the corresponding film strip 66 with a force corresponding to the strength of the hand as a whole.

Additional spacers (not shown) may be inserted between the spacer 69 and the vertical plate 12b to accommodate larger hand sizes.

The film strips are pressure-sensitive so as to indicate the pressures applied to them by the dowels, and thereby the strengths to be measured.

The pressure-sensitive film used is Fuji Super Low Prescale Film, manufactured and marketed by the Fuji Photo Film Co., Ltd. It is composed of an "A-film," coated with a layer of microcapsulated color-forming material, and a "C-film" coated with a layer of color developing material. In order to carry out pressure measurement, the A. and C-films are superimposed with the coated sides face to face. Upon application of pressure, the microcapsules on the A-film are broken and the released color-forming material reacts with the color developing material to generate a color on the C-film. The microcapsule layer (on the A-film) consists of microcapsules of various sizes. Larger microcapsules can be broken by a weaker pressure, while smaller ones require a stronger pressure for breakage. An exact relationship between the applied pressure and the developed color is realized by the precise control of capsule size, size distribution and capsule wall thickness. Thus, the developed color not only provides graphic presentation of pressure distribution, but will also determine pressure either by measurement with a densitometer or by direct comparison with a set of standard color samples.

Figure 4:
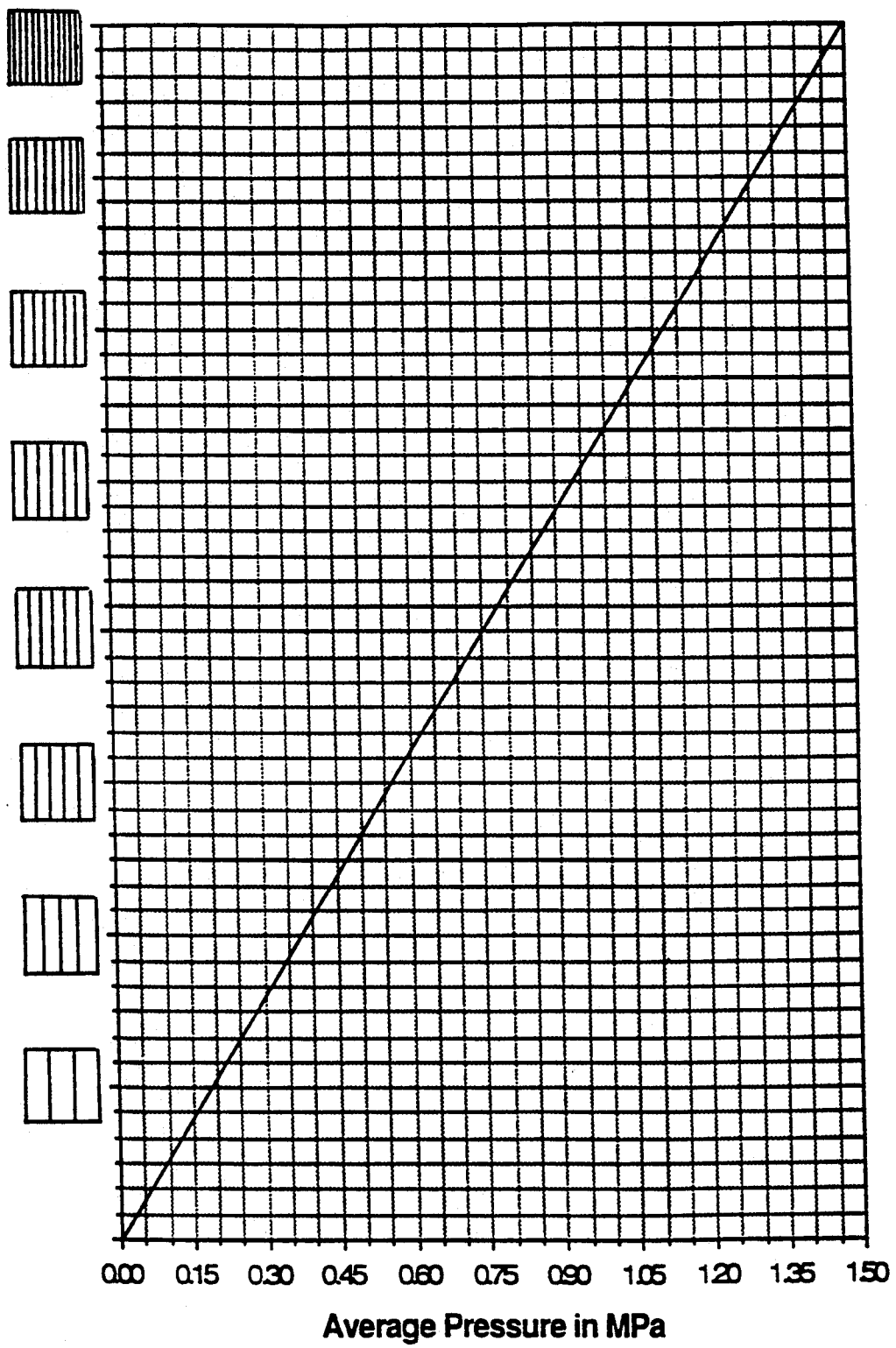
FIG. 4 is a Fuji Super Low Prescale Film Calibration Chart illustrating characteristics of a film that can be used with the precision grip meter of FIG. 1.

The calibration chart of FIG. 4 was developed by the inventors and provides standard color samples for the Fuji Super Low Prescale Film. These standard color samples, produced with actual samples of Fuji Super Low Prescale Film (rather than as in the Fuji Co. instruction manual, where conventional printing techniques do not reproduce the speckled appearance of the actual film), provide for accurate comparison and extrapolation of the color density produced on the film strips, and thereby indicate the pressures exerted on experimental film samples. Therefore, the samples can be used as a calibration chart for reading pressure directly from the colors produced on the film strips.

The calibration chart of FIG. 4 is organized with the standard color samples on the vertical axis and the corresponding pressure readings on the horizontal axis The standard color samples represent the average color densities of four experimental trials. A best fit, linear curve plotted from the experimental data is used to determine pressure readings from experimental samples. Since each microcapsule releases the same color, bright red, comparisons between standard and experimental samples must be based on the color density. Color density is calculated by the number of bright red dots in a given area.

When an experimental sample is developed it is compared to the standard color samples on the vertical axis of the chart. Comparisons are based on the color density close to the center of the standard samples. The film tends to darken near the edge of the object that applies the pressure to the film.

Although the heights of the standard color samples span several of the chart's horizontal lines, the color samples actually correspond to one particular line near the center of each color sample. Readings may have to be interpolated so as to represent the actual pressure exerted on the film. Therefore, if an experimental sample does not match any of the standard samples, one must interpolate between the two closest standard samples using the added horizontal lines on the chart.

Once a horizontal line is selected which represents the color density of the experimental sample, the line is followed horizontally on the chart to intersect the curve. Then, vertically below that intersection point on the chart, the corresponding pressure reading is found on the average pressure axis. The smallest increment on the horizontal axis is 0.05 MPa. However, interpolation may be used to estimate pressure more precisely.

It has been found that the Fuji film tends to darken near the edge of the object that applied the pressure to the film. To avoid this edge effect, means for evenly spreading the pressure exerted by each dowel may be provided. For example, a piece of rubber tape or an elastic pad, for example, may be placed on the face of each dowel that contacts the film, as seen at 24a and 37a in FIG. 2, for example.

Although the present invention has been described in relation to particular embodiments thereof, the fair scope of the claims will include many other variations and modifications and other uses which will become apparent to those skilled in the art. Accordingly, the present invention is not to be considered as being limited by the specific disclosures herein.

What is claimed is:

1. A device for measuring and recording the strength of a person's hand that includes:
   a frame;
   a base on the frame sized and shaped to engage the heel of the hand; .
   a plurality of plungers on the frame opposite the base and located for being depressed by corresponding fingers of the hand; and
   a device associated with the base and the plungers for simultaneously and independently measuring and recording both finger strength and overall hand strength.

2. A device as in claim 1, wherein said base and plungers are configured and arranged for measuring and recording the strength of either a left hand or a right hand.

3. A device as in claim 1, wherein said device comprises respective photographic pressure-sensitive films operatively engaged with said base and said plungers.

4. A grip strength meter according to claim 3, wherein said films employ exclusively chemical means to produce visual indications of said finger and hand strength.

5. A grip strength meter comprising
   a frame;

force-detecting means;

first means on the frame for receiving the fingers of a hand and applying force exerted by said fingers to said force-detecting means; and second means on the frame for receiving the heel of the hand and applying force exerted by said heel to said force-detecting means;

wherein said first means comprises a plurality of plungers movably mounted on the frame for independent movement in a direction inwardly of said frame in response to force exerted by said fingers, said force-detecting means being responsive to said movement of said plungers for measuring the individual strength of each finger; and wherein said second means comprises a base movably mounted on the frame for movement in a direction inwardly of said frame in response to force exerted by said eel, said force-detecting means being responsive to said movement of said base for measuring overall hand strength independently of individual finger strength.

6. A grip strength meter as in claim 5 wherein said force-detecting means comprises photographic sensitive film and means for mounting said film on said frame for being engaged by said plungers and said base in response to said movement thereof.

7. A grip strength meter as in claim 6 wherein said force-detecting means comprises a first film and first means for mounting said first film on said frame for being engaged by said plungers, and a separate second film and second means for mounting said second film on said frame for being engaged by said base.

8. A grip strength meter as in claim 7, wherein said first and second mounting means respectively comprise first and second cartridges for holding said first and second films for engagement with and removal from said grip strength meter.

9. A grip strength meter according to claim 6, wherein said film employs exclusively chemical means to produce visual indications of said finger and hand strength.

10. A grip strength meter according to claim 7, wherein said films employ exclusively chemical means to produce visual indications of said finger and hand strength.

* * * * *